United States Patent [19]
Kotek

[11] Patent Number: 5,294,707
[45] Date of Patent: Mar. 15, 1994

[54] SEMI-CONTINUOUS DEPOLYMERIZATION OF NYLON 6 POLYMER

[75] Inventor: Richard Kotek, Arden, N.C.

[73] Assignee: BASF Corporation, Parsippany, N.J.

[21] Appl. No.: 23,030

[22] Filed: Feb. 25, 1993

[51] Int. Cl.$^5$ .......................................... C07D 201/12
[52] U.S. Cl. ................................................ 540/540
[58] Field of Search ...................................... 540/540

[56] References Cited

U.S. PATENT DOCUMENTS

| | | | |
|---|---|---|---|
| 3,182,055 | 5/1965 | Bonfield et al. | 340/540 |
| 3,939,153 | 2/1976 | Fowler | 540/540 |
| 4,107,160 | 8/1978 | Dicoi et al. | 540/540 |
| 4,605,762 | 8/1986 | Mandoki | 340/540 |
| 4,620,032 | 10/1986 | Doerr | 540/540 |

FOREIGN PATENT DOCUMENTS 60-20379 of 1985 Japan .............................. 540/540

OTHER PUBLICATIONS

F. Mikula, K. Petru, "The Depolymerization of Polycaprolactam Wastes to Monomeric 6-Caprolactam", *Chemicky Prumysl.* 17, 1967, pp. 132-137.

L. A. Dmitrieva, A. A. Speranskii, S. A. Krasavin, Y. N. Bychkov, "Regeneration of Epsilon-Caprolactam From Wastes in the Manufacture of Polycaproamide Fibres and Yarns", Fibre Chemistry, Mar., 1986. (translated from Khimicheskie Volokna, No., 4, pp. 5-12, Jul.-Aug, 1985).

A. A. Ogale, "Depolymerization of Nylon 6: Some Kinetic Modeling Aspects", Journal of Applied Polymer Science, vol. 29, 1984, pp. 3947-3954.

I. Mladenov, T. Vladkova, S. Fakirov, A. Mitsulov, "X-Ray Diffraction and IR Spectroscopie Investigation of the Products of the Reaction Between Poly-ξ-Capro-amide and Ortho-Phosphoric Acid", *Pol. Sci. USSR*, vol. No. 20, 1978, pp. 341-346.

Takashi Ohtsubo, Yasuchi Hamanaka, Yukihiro Hokamura, Toshifumi Ohnishi, "Repeated Batch-Wise Depolymerization of Polycaproamide Catalyzed by Phosphoric Acid Under Steam Blowing", *J. Chem. Soc, Jap. Chem. Ind.*, No. 10, 1975, pp. 1834-1837.

*Primary Examiner*—Robert T. Bond
*Attorney, Agent, or Firm*—Karen M. Dellerman

[57] ABSTRACT

Polyamide is semi-continuously depolymerized by: (a) charging the polyamide to a depolymerization reactor containing 5 to 50% by weight of an unpolymerized catalyst; (b) melting the polyamide and subjecting the resultant melt to a flow of superheated steam to obtain a steam distillate; (c) separating amide monomers in the distillate from other volatiles therein; (d) when conversion to amide monomers is 40 to 90% complete, recharging polyamide to the depolymerization reactor; and (e) repeating steps (a)-(d) until a desired amount of polyamide is depolymerized.

8 Claims, No Drawings

SEMI-CONTINUOUS DEPOLYMERIZATION OF NYLON 6 POLYMER

FIELD OF THE INVENTION

This invention relates generally to the catalytic depolymerization of polycondensation polymers. More particularly, this invention relates to semi-continuous catalytic depolymerization of polyamides.

BACKGROUND OF THE INVENTION

As used herein the term "semi-continuous process" means a process where polyamide is periodically recharged to a depolymerization reactor after the previous charge is partially exhausted.

Large quantities of polymeric waste accumulate from polymer processing and post-consumer waste. Recycling and reuse of materials is an ever-growing topic of research and development. Any process which enhances the ability to reclaim reusable materials from waste has extreme value. It is generally known that polycondensation products, like polyamides, can be depolymerized to some or all of the backbone monomers.

Processes for depolymerizing nylon 6 are known. F. Mikula, K. Petru, "The Depolymerization of Polycaprolactam Wastes to Monomeric 6-Caprolactam", *Chemicky Prumysl*, 17, 1967, pp. 132-137, describe a process for catalytically depolymerizing nylon 6 to $\epsilon$-caprolactam. Boric acid (and derivatives) is the authors' preferred catalyst due to experiments showing a better depolymerization rate than with phosphoric acid. Catalysts are charged at up to 1.0%.

L. A. Dmitrieva, A. A. Speranskii, S. A. Krasavin and Y. N. Bychkov, "Regeneration of $\epsilon$-Caprolactam From Wastes In the Manufacture of Polycaproamide Fibres and Yarns", *Fibre Chemistry*, March 1986, (translated from Khimicheskie Volokna, No. 4, pp. 5-12, July-August, 1985) is a literature review describing processes for depolymerizing nylon 6 with and without using a catalyst.

Nylon 6 depolymerization kinetics are described by A. A. Ogale, "Depolymerization of Nylon 6:Some Kinetic Modeling Aspects", *Journal of Applied Polymer Science*, Vol. 29, 1984, pp. 3947-3954. Relatively low concentrations (0.2 to 1.05%) of catalysts were used.

Numerous disadvantages and problems with catalyzed nylon 6 depolymerization have been disclosed. For example, U.S. Pat. No. 3,939,153 to Fowler discloses a non-catalytic depolymerization process to resolve the consumption of ortho-phosphoric catalyst and consequent decrease in the rate of caprolactam recovery. I. Mladenov, T. Vladkova, S. Fakirov and A. Mitsulov, "X-Ray Diffraction and IR Spectroscopic Investigation of the Products of the Reaction Between Poly-$\epsilon$-Capro-amide and Ortho-Phosphoric Acid", *Pol. Sci. USSR*, Vol No. 20, 1978 pp. 341-346, indicate the formation of oligoamidophosphates.

Takashi Ohtsubo, Yasuchi Hamanaka, Yukihiro Hokamura and Toshifumi Ohnishi, "Repeated Batch-Wise Depolymerization of Polycaproamide Catalyzed by Phosphoric Acid Under Steam Blowing", *J. Chem. Soc. Jap., Chem. Ind.*, No. 10, 1975, pp. 1834-1837, indicate the formation of pyrophosphoric acid. It is known that ortho-phosphoric acid polymerizes at high temperatures. Formation of polyphosphoric acid gradually deactivates the catalyst and could have additional adverse effects such as an increase of polymer melt viscosity. High viscosity media may reduce the reaction rate also. Therefore, the process described is slow and suitable for batch-type depolymerization of nylon 6 waste without solid contaminants but not for repetitive reactor recharging.

Various versions of catalytic depolymerization of nylon 6 have been described. U.S. Pat. No. 3,182,055 to Bonfield describes the progressive addition of ortho-phosphoric acid and nylon 6. U.S. Pat. No. 4,605,762 to Mandoki describes hydrolytic depolymerization of condensation polymers without any catalyst. U.S. Pat. No. 4,620,032 to Doerr describes shortened depolymerization reaction time by using pre-molecular weight reduction agents. U.S. Pat. No. 4,107,160 to Dicoi discloses a fully continuous process for depolymerizing nylon 6 scrap using about 2-3% of phosphoric acid. Japanese Tokyo Koho No. 60 20,379 assigned to Toyobo discloses a process for depolymerizing nylon 6 using 0.2% $H_3PO_4$.

While continuous depolymerization of nylon 6 wastes could offer high productivity, the efficiency of such continuous process can be dramatically reduced in the presence of contaminants. Furthermore amides or polyamides are known to hardly hydrolyze, thus the artisan is always faced with a limited degree of flexibility in the efficient depolymerization of nylon 6.

SUMMARY OF THE INVENTION

The shortcomings in the processes described above are met in a process for the semi-continuous depolymerization of a polyamide (having a melting point) by (a) charging the polyamide to a depolymerization reactor containing 5 to 50% by weight of an unpolymerized catalyst; (b) melting the polyamide and subjecting the resultant melt to a flow of superheated steam to obtain a steam distillate; (c) separating amide monomers in the distillate from other volatiles therein; and (d) when conversion to amide monomers is 40 to 90% complete, recharging polyamide to the depolymerization reactor; and repeating steps (a)-(d) until a desired amount of polyamide is depolymerized.

It is an object of the present invention to provide a semi-continuous process for depolymerizing polyamides.

Related objects and advantages will be apparent to those of ordinary skill in the art after reading the following detailed description.

DETAILED DESCRIPTION OF THE PREFERRED EMBODIMENTS

To promote an understanding of the principles of the present invention, descriptions of specific embodiments of the invention follow, and specific language describes the same. It will nevertheless be understood that no limitation of the scope of the invention is thereby intended, and that such alterations and further modifications, and such further applications of the principles of the invention as discussed are contemplated, as would normally occur to one ordinarily skilled in the art to which the invention pertains.

A semi-continuous process has been found for the catalytic depolymerization of solid condensation polymer wastes. In addition to a high depolymerization efficiency, the new process offers reduction of acid catalyst wastes. In accordance with this invention, the process involves the use of unpolymerized catalysts such as p-toluenesulfonic or ortho-phosphoric acid at a relatively high concentration in the range from 5 to 50%. The depolymerization is carried out to a relatively low degree of conversion before recharging the depolymerization reactor with a new batch of nylon 6 waste.

The invention is particularly useful with polyamides. The preferred polyamides are those made from a single monomer. However, copolymers may also be depolymerized according to the invention. The process is preferred for use with nylon 6 to recover $\epsilon$-caprolactam. Polymer wastes which may be treated in accordance with the present invention are not limited by form and may be in various forms such as molded articles, chips, fibers, film and the like. The invention is particularly suitable for polymer wastes containing solid contaminants such as pigments, $TiO_2$, pigment carriers such as polyethylene and other solid contaminations.

The semi-continuous depolymerization may be carried out in any acid resistant conventional reactor equipped with a condenser and an inlet for loading polyamides. The reactor may be equipped with a stirrer and nozzles for supplying steam, which may be used as a carrier for removing $\epsilon$-caprolactam from the depolymerization mixture. Molten or solid polyamide waste can be added through the inlet of the reactor. Preferably, the reactor is purged with nitrogen or some other inert atmospheres, during the addition of polymer wastes. Some catalysts are more sensitive to oxygen than others. Therefore, some care should be taken to exclude oxygen from the system. Preferably a catalyst should be added as a solution in water. The catalyst concentration in solution is not thought to be critical, however, the preferred concentration is in the range of from 40 to 85%.

In an exemplary semi-continuous depolymerization process, an electrically heated reactor, preferably stainless steel, is charged by feeding the ground polymer waste on a conveyer belt and with an acid catalyst usually at the load from about 5 to about 50%. Then the reactor is heated to a temperature between about 260° to 280° C. and superheated steam having a temperature between about 100° C. and about 450° C. is injected into the reactor below the polymer melt. The caprolactam volatiles formed are directed along with the steam to a condenser. The resulting caprolactam distillate is collected in a tank for further processing. Usually the depolymerization progress is monitored by the determination of the caprolactam content in the distillate. When about 40 to 90% conversion is reached, a new batch of polymer waste is loaded and the process is continued.

The depolymerization process is preferably carried out at a polymer melt temperature of at least 25° C. above the melting point of the polymer but not higher than 320° C. While higher temperatures may increase reaction rates, the higher temperatures may lead to significant amounts of impurities in the regenerated monomer. For example, where the polymer is nylon 6 which has a melting point of about 223° C., the process preferably is carried out at 270° C.

The preferable degree of conversion before a recharge of polymer is 40 to 90%. For catalysts which are polymerizable, the degree of conversion prior to recharge is preferably 40 to 85%. For non-polymerizable catalysts, the degree of conversion is preferably 75 to 90%.

A variety of catalysts are useful in practicing the invention. Non-polymerizable inorganic or organic acids such as boric acid, xylenesulfonic acid, 4-sulfoisophthalic acid and other sulfonated aromatic hydrocarbons can be employed in the present invention. Polymeric catalysts, like polyphosphoric acid, are generally unsuitable. Especially preferred catalysts are orthophosphoric and p-toluenesulfonic acids. For orthophosphoric acid, the preferred concentration is 5 to 25%. Catalyst loads in the range of 10 to 35% are preferred for p-toluenesulfonic acid. These high catalyst loads allow nylon 6 to break into substituent monomers more easily, producing less by-products and consequently increasing depolymerization rates. Catalysts should be relatively free from impurities or discoloration of the monomer may result.

In comparison to a batch process, the process of the invention offers reduction of catalyst wastes. To illustrate, assume that each waste charge has 100 parts using 1.5 parts catalyst for each load in a batch process and a one-time catalyst load of 15 parts in the semi-continuous process of this invention. So if the batch process is conducted 50 times, the amount of catalyst used is 75 parts. Since the amount of catalyst in the process of the present invention is only 15 parts, there is a five-fold reduction of the catalyst wastes. A batch depolymerization process requires a new load of catalyst for each load of nylon 6 waste. In the semi-continuous process of the present invention, only a single load of the catalyst is needed.

Two analytical techniques, gas chromatography (GC) and the refractive index method, are especially suitable to monitor the depolymerization progress of nylon 6 polymer. The latter method is used in the following Examples for determination of $\epsilon$-caprolactam content and GC is employed to determine the purity of the regenerated caprolactam.

GC METHOD

A Varian Vista Model 6000 gas chromatograph is equipped with flame ionization detector and a Nukol megabore (15 mm×0.53 ID, 0.5 $\mu$m film thickness) column. Helium at 15–18 mL/min is the carrier gas. The injector temperature is maintained at 280° C. and the detector temperature at 280° C. The column temperature is 165° C.

A standard calibration curve is prepared by plotting caprolactam peak area versus concentration for a series of working standards ranging in caprolactam concentration from 0.01% to 1%. Experimental samples are prepared by diluting the samples until the caprolactam concentration is less than 1%, keeping track of the dilutions made.

Using a 10 $\mu$L syringe, 1 $\mu$L of each standard is injected into the GC using the column and conditions described above. Each standard is injected twice and the caprolactam peak area is recorded. The average of both peak heights is used for plotting a standard calibration curve. One (1) $\mu$L of each sample is injected twice and the peak area recorded and averaged. The concentration of caprolactam is read directly against the calibration curve. This concentration is then corrected by the dilution factor of each sample.

REFRACTIVE INDEX METHOD

Bausch & Lomb refractometer is used at 25° C.

The dependence between the monomer content and refractive index is given in Table 1 below:

TABLE 1

| $\epsilon$-Caprolactam Concentration (wt. %) | Refractive Index |
|---|---|
| 0 | 1.3320 |

TABLE 1-continued

| ε-Caprolactam Concentration (wt. %) | Refractive Index |
|---|---|
| 1 | 1.3335 |
| 5 | 1.3402 |
| 10 | 1.3478 |
| 20 | 1.3640 |
| 30 | 1.3805 |

The invention will be described by referring to the following detailed examples. These examples are set forth by way of illustration and are not intended to be limiting in scope.

EXAMPLE 1

Semi-continuous Depolymerization of Nylon 6 With p-Toluenesulfonic Acid As A Catalyst A glass reactor is equipped with a condenser, an inlet and a receiver. This reactor is initially charged with 200 grams of nylon 6 waste and 10% by weight of p-toluenesulfonic acid as a 50% aqueous solution and heated to a temperature of 270° C. When the target melt temperature is reached, steam is injected below the polymer melt to steam distill ε-caprolactam from the depolymerization mixture. The steam flow rate is controlled at 3 to 7 g/min. The steam distillate is collected. The degree of conversion is monitored by the refractive index of the steam distillate. After reaching a conversion of approximately 50%, the reactor is recharged with new additions of nylon 6 waste as described in Table 2 below. The depolymerization is monitored by measuring the refractive index of the distillate and reported in Table 2 below.

TABLE 2

Initial Charge:

| Time (min) | Refractive Index | Caprolactam Concentration (%) | Cumulative Caprolactam Recovered (%) | Remarks |
|---|---|---|---|---|
| 0 | 1.3576 | 15.92 | 1.16 | Steam injected when melt reached 270° C. |
| 15 | 1.3724 | 25.09 | 11.52 | |
| 30 | 1.3540 | 13.69 | 16.05 | |
| 45 | 1.3566 | 15.30 | 22.57 | |
| 60 | 1.3568 | 15.42 | 29.71 | |
| 75 | 1.3570 | 15.54 | 37.85 | |
| 90 | 1.3564 | 15.17 | 45.32 | |
| 105 | 1.3564 | 15.17 | 52.43 | |

Addition No. 1: Amount nylon 6 added 100 grams
Total amount of nylon 6 in vessel 195.14 grams

| Time (min) | Refractive Index | Caprolactam Concentration (%) | Cumulative Caprolactam Recovered (%) | Remarks |
|---|---|---|---|---|
| 0 | 0 | 0 | 0 | No steam present during nylon 6 addition. |
| 15 | 1.3707 | 24.03 | 11.26 | |
| 30 | 1.3544 | 13.93 | 16.85 | |
| 45 | 1.3555 | 14.61 | 21.87 | |
| 60 | 1.3602 | 17.53 | 26.22 | |
| 105 | 1.3515 | 12.14 | 46.42 | |

Addition 2: Amount of nylon 6 added 100 grams
Total amount of nylon 6 in vessel 204.56 grams

| Time (min) | Refractive Index | Caprolactam Concentration (%) | Cumulative Caprolactam Recovered (%) | Remarks |
|---|---|---|---|---|
| 0 | 1.3447 | 7.92 | 3.35 | Steam present during nylon 6 addition. Low polymer melt viscosity Clear distillate. |
| 15 | 1.3525 | 12.76 | 8.86 | |
| 30 | 1.3442 | 7.61 | 13.70 | |
| 45 | 1.3448 | 7.98 | 19.23 | |
| 60 | 1.3512 | 11.95 | 25.48 | |
| 75 | 1.3505 | 11.52 | 32.00 | |
| 90 | 1.3507 | 11.64 | 39.79 | |
| 105 | 1.3584 | 16.41 | 46.86 | |

Addition No. 3: Amount of nylon 6 added 100 grams
Total amount of nylon 6 in vessel 208.70 grams

| Time (min) | Refractive Index | Caprolactam Concentration (%) | Cumulative Caprolactam Recovered (%) | Remarks |
|---|---|---|---|---|
| 0 | 1.3382 | 3.89 | 1.65 | After 45 min. stopped and left the vessel open at 100° C. overnight. Some yellow distillate after reheating to 270° C. |
| 15 | 1.3498 | 11.08 | 7.02 | |
| 30 | 1.3642 | 20.01 | 17.53 | |
| 45 | 1.3432 | 6.99 | 21.92 | |
| 60 | 1.3458 | 8.60 | 26.61 | |
| 75 | 1.3463 | 8.91 | 31.38 | |
| 105 | 1.3486 | 10.34 | 42.15 | |
| 135 | 1.3492 | 10.71 | 46.92 | |
| 150 | 1.3482 | 10.09 | 49.04 | |

Addition No. 4: Amount of nylon 6 added 100 grams
Total amount of nylon 6 in vessel 206.35 grams

| Time (min) | Refractive Index | Caprolactam Concentration (%) | Cumulative Caprolactam Recovered (%) | Remarks |
|---|---|---|---|---|
| 0 | 0 | 0 | 0 | Steam present during nylon 6 addition. Decided to use stream in the next additions of nylon 6. |
| 75 | 1.3472 | 9.47 | 20.95 | |
| 120 | 1.3476 | 9.72 | 36.24 | |
| 180 | 1.3486 | 10.34 | 52.24 | |

Addition No. 5: Amount of nylon 6 added 100 grams
Total amount of nylon 6 in vessel 198.55 grams

| Time (min) | Refractive Index | Caprolactam Concentration (%) | Cumulative Caprolactam Recovered (%) | Remarks |
|---|---|---|---|---|
| 0 | 0 | 0 | 0 | Stopped after 150 min. Added 100 grams nylon 6. Cooled down under nitrogen purge to avoid distillate yellowing. |
| 60 | 1.3456 | 8.48 | 14.68 | |
| 120 | 1.3465 | 9.04 | 34.06 | |
| 160 | 1.3485 | 10.28 | 46.71 | |

Addition No. 6: Amount of nylon 6 added 100 grams
Total amount of nylon 6 in vessel 205.81 grams

| Time (min) | Refractive Index | Caprolactam Concentration (%) | Cumulative Caprolactam Recovered (%) | Remarks |
|---|---|---|---|---|
| 0 | 1.3330 | 0.67 | 0.6 | No yellow distillate. Low polymer melt viscosity. Polymer melt is dark |
| 60 | 1.3450 | 8.11 | 17.76 | |
| 120 | 1.3480 | 9.97 | 32.13 | |
| 180 | 1.3476 | 9.72 | 52.02 | |

Addition No. 7: Amount of nylon 6 added 100 grams
Total amount of nylon 6 in vessel 198.75 grams

| Time (min) | Refractive Index | Caprolactam Concentration (%) | Cumulative Caprolactam Recovered (%) |
|---|---|---|---|
| 0 | 0 | 0 | 0 |
| 60 | 1.3492 | 10.71 | 18.33 |
| 120 | 1.3486 | 10.34 | 37.02 |
| 180 | 1.3484 | 10.22 | 54.61 |

Addition No. 8: Amount of nylon 6 added 100 grams
Total amount of nylon 6 in vessel 190.21 grams

| Time (min) | Refractive Index | Caprolactam Concentration (%) | Cumulative Caprolactam Recovered (%) | Remarks |
|---|---|---|---|---|
| 0 | 1.3382 | 3.89 | 3.78 | Clear distillate. Low polymer melt viscosity. |
| 60 | 1.3445 | 7.80 | 18.67 | |
| 120 | 1.3450 | 8.11 | 38.14 | |
| 150 | 1.3455 | 8.42 | 47.73 | |

Addition No. 9: Amount nylon 6 added 100 grams
Total amount of nylon 6 in vessel 199.42 grams

| Time (min) | Refractive Index | Caprolactam Concentration (%) | Cumulative Caprolactam Recovered (%) |
|---|---|---|---|
| 0 | 0 | 0 | 0 |
| 60 | 1.3427 | 6.68 | 15.82 |
| 120 | 1.3442 | 7.61 | 32.28 |
| 180 | 1.3464 | 8.98 | 50.49 |

EXAMPLE 2

Semi-continuous Depolymerization of Nylon 6 With Phosphoric Acid As A Catalyst

The reactor described in Example 1 is charged with 200 grams of nylon 6 waste and 10% of ortho-phosphoric acid as an 85% solution and heated to 270° C. The trial is conducted as described in Example 1 except for the degree of conversion which is varied from 41.5 to 68.6%. The results are reported in Table 3 below.

TABLE 3

Initial Charge:

| Time (min) | Refractive Index | Caprolactam Concentration (%) | Cumulative Caprolactam Recovered (%) | Remarks |
|---|---|---|---|---|
| 0 | 0 | 0 | 0 | Steam injected when melt reached 270° C. Steam present during all additions of nylon 6. |
| 60 | 1.3624 | 18.89 | 44.26 | |
| 75 | 1.3682 | 22.48 | 62.61 | |

Addition No. 1: Amount of nylon 6 added 100 grams
Total amount of nylon 6 in vessel 174.78 grams

| Time (min) | Refractive Index | Caprolactam Concentration (%) | Cumulative Caprolactam Recovered (%) |
|---|---|---|---|
| 0 | 0 | 0 | 0 |
| 75 | 1.3638 | 19.76 | 68.58 |

Addition No. 2: Amount of nylon 6 added 150 grams
Total amount of nylon 6 in vessel 204.9 grams

| Time (min) | Refractive Index | Caprolactam Concentration (%) | Cumulative Caprolactam Recovered (%) |
|---|---|---|---|
| 0 | 0 | 0 | 0 |
| 60 | 1.3553 | 14.49 | 42.19 |
| 75 | 1.3674 | 21.99 | 60.99 |

Addition No. 3: Amount of nylon 6 added 100 grams
Total amount of nylon 6 in vessel 179.93 grams

| Time (min) | Refractive Index | Caprolactam Concentration (%) | Cumulative Caprolactam Recovered (%) |
|---|---|---|---|
| 0 | 0 | 0 | 0 |
| 75 | 1.3614 | 18.27 | 74.12 |

| Addition No. 4: Amount of nylon 6 added 150 grams<br>Total amount of nylon 6 in vessel 196.75 grams ||||
|---|---|---|---|
| Time (min) | Refractive Index | Caprolactam Concentration (%) | Cumulative Caprolactam Recovered (%) |
| 0 | 0 | 0 | 0 |
| 75 | 1.3645 | 20.19 | 68.86 |

| Addition No. 5: Amount of nylon 6 added 150 grams<br>Total amount of nylon 6 in vessel 211.27 grams ||||
|---|---|---|---|
| Time (min) | Refractive Index | Caprolactam Concentration (%) | Cumulative Caprolactam Recovered (%) |
| 0 | 0 | 0 | 0 |
| 75 | 1.3562 | 15.05 | 41.52 |

| Addition No. 6: Amount of nylon 6 added 100 grams<br>Total amount of nylon 6 in vessel 223.55 grams ||||
|---|---|---|---|
| Time (min) | Refractive Index | Caprolactam Concentration (%) | Cumulative Caprolactam Recovered (%) |
| 0 | 0 | 0 | 0 |
| 75 | 1.365 | 20.5 | 45.87 |

| Addition No. 7: Amount of nylon 6 added 100 grams<br>Total amount of nylon 6 in vessel 221 grams ||||
|---|---|---|---|
| Time (min) | Refractive Index | Caprolactam Concentration (%) | Cumulative Caprolactam Recovered (%) |
| 0 | 0 | 0 | 0 |
| 75 | 1.3596 | 17.16 | 50.66 |

| Addition No. 8: Amount of nylon 6 added 100 grams<br>Total amount of nylon 6 in vessel 209 grams ||||
|---|---|---|---|
| Time (min) | Refractive Index | Caprolactam Concentration (%) | Cumulative Caprolactam Recovered (%) |
| 0 | 0 | 0 | 0 |
| 75 | 1.3577 | 15.98 | 52.34 |

| Addition No. 9: Amount of nylon 6 added 125 grams<br>Total amount of nylon 6 in vessel 224.6 grams ||||
|---|---|---|---|
| Time (min) | Refractive Index | Caprolactam Concentration (%) | Cumulative Caprolactam Recovered (%) |
| 0 | 0 | 0 | 0 |
| 75 | 1.3596 | 17.16 | 45.2 |

| Addition No. 10: Amount of nylon 6 added 125 grams<br>Total amount of nylon 6 in vessel 248.08 grams ||||
|---|---|---|---|
| Time (min) | Refractive Index | Caprolactam Concentration (%) | Cumulative Caprolactam Recovered (%) |
| 0 | 0 | 0 | 0 |
| 60 | 1.3619 | 18.58 | 39.47 |
| 75 | 1.3548 | 14.18 | 48.38 |

EXAMPLE 3

(Comparative)-Polymeric Catalyst

The technique used in Example 1 is followed to depolymerize nylon 6 but with the use of 5% of polyphosphoric acid at 270° C. The catalyst has a $P_2O_5$ content of 85.3%. The polymer melt viscosity is exceptionally high and practically is not changed even after prolonged heating. No $\epsilon$-caprolactam is collected.

EXAMPLE 4

4-Sulfophthalic Acid As A Catalyst

The technique used in Example 1 is used to depolymerize nylon 6 with 10% 4-sulfophthalic acid at 270° C. The catalyst concentration in water is 50%. The polymer melt viscosity remains relatively high and the melt is dark brown. The distillates collected are discolored in comparison to the clear distillates from Examples 1 and 2. The conversion was about 90% after 2 hours.

EXAMPLE 5

Xylenesulfonic Acid As A Catalyst

The technique used in Example 1 is used to depolymerize nylon 6 with 5% xylenesulfonic acid at 270° C. The catalyst concentration in water is 22%. The polymer melt viscosity remains relatively high and the melt is dark brown. All distillates collected are cloudy and exhibit an unpleasant odor. As shown in Table 4 below, the depolymerization yield is 48.2% after 210 minutes.

TABLE 4

| Time (min) | Refractive Index | Caprolactam Concentration (%) | Cumulative Caprolactam Recovered (%) |
|---|---|---|---|
| 0 | 1.3364 | 2.78 | 0.54 |
| 15 | 1.3590 | 16.78 | 4.44 |
| 30 | 1.3574 | 15.79 | 8.69 |
| 45 | 1.3512 | 11.95 | 11.69 |
| 60 | 1.3480 | 9.97 | 16.65 |
| 75 | 1.3472 | 9.47 | 21.72 |
| 90 | 1.3440 | 7.49 | 27.03 |
| 210 | 1.3440 | 7.49 | 48.22 |

EXAMPLE 6

Boric Acid As A Catalyst

A reactor described in Example 1 is charged with 200 grams of nylon 6 waste and 15% aqueous boric acid. The catalyst concentration in water is 20%. The system is heated to 300° C. before injecting steam below the polymer melt. The melt viscosity is extremely low at the beginning but progressively increases. The yield is 55.7% after 150 minutes (see Table 5 below).

TABLE 5

| Time (min) | Refractive Index | Caprolactam Concentration (%) | Cumulative Caprolactam Recovered (%) |
|---|---|---|---|
| 0 | 1.3392 | 4.51 | 2.06 |
| 15 | 1.3745 | 26.39 | 11.95 |
| 30 | 1.3642 | 20.01 | 19.76 |
| 45 | 1.3595 | 17.09 | 26.39 |
| 60 | 1.3556 | 14.68 | 33.21 |
| 75 | 1.3426 | 6.62 | 36.20 |
| 90 | 1.3485 | 10.28 | 43.35 |
| 105 | 1.3454 | 8.36 | 46.62 |
| 120 | 1.3437 | 7.30 | 51.76 |
| 150 | 1.3390 | 4.39 | 55.74 |

What is claimed is:

1. A process for the semi-continuous depolymerization of nylon 6 comprising:
    (a) charging nylon 6 to a depolymerization reactor containing 5 to 50% by weight of unpolymerized catalyst;
    (b) melting the nylon 6 and subjecting the resultant melt to a flow of superheated steam to obtain a stream distillate;
    (c) separating caprolactam monomers in the distillate from other volatiles therein;
    (d) when conversion to caprolactam is 40 to 90% complete, recharging nylon 6 to the depolymerization reactor; and
    (e) repeating steps (a)–(d) until a desired amount of nylon 6 is converted to caprolactam.

2. The process of claim 1 wherein said charging is to a depolymerization reactor containing a catalyst selected from the group consisting of ortho-phosphoric acid and p-toluenesulfonic acid.

3. The process of claim 1 wherein said melting is to at least 270° C.

4. The process of claim 1 wherein said charging is to a depolymerization reactor containing an ortho-phosphoric acid catalyst.

5. The process of claim 4 wherein said recharging is when conversion to amide monomers is 40 to 85% complete.

6. The process of claim 4 wherein said charging is to a depolymerization reactor containing 5 to 25% by weight of catalyst.

7. The process of claim 1 wherein said charging is to a depolymerization reactor containing a p-toluenesulfonic acid catalyst.

8. The process of claim 7 wherein said recharging is when conversion to caprolactam monomers is 70 to 90% complete.

* * * * *